United States Patent
Rossignoli et al.

(10) Patent No.: US 12,351,826 B2
(45) Date of Patent: Jul. 8, 2025

(54) METHOD TO PRODUCE CONDITIONALLY APOPTOTIC CELLS

(71) Applicant: EIR BIOTHERAPIES SRL, Mirandola (IT)

(72) Inventors: Filippo Rossignoli, Verona (IT); Carlotta Spano, Modena (IT); Giulia Grisendi, Reggio Emilia (IT); Olivia Candini, Crevalcore (IT); Massimo Dominici, Ferrara (IT)

(73) Assignee: RIGENERAND S.R.L., Medolla (IT)

( * ) Notice: Subject to any disclaimer, the term of this patent is extended or adjusted under 35 U.S.C. 154(b) by 920 days.

(21) Appl. No.: 17/058,911

(22) PCT Filed: May 31, 2019

(86) PCT No.: PCT/IT2019/050123
§ 371 (c)(1),
(2) Date: Nov. 25, 2020

(87) PCT Pub. No.: WO2019/229782
PCT Pub. Date: Dec. 5, 2019

(65) Prior Publication Data
US 2021/0214689 A1 Jul. 15, 2021

(30) Foreign Application Priority Data
Jun. 1, 2018 (IT) .................. 102018000005951

(51) Int. Cl.
*C12N 5/0775* (2010.01)
*C12N 15/63* (2006.01)

(52) U.S. Cl.
CPC ........... *C12N 5/0667* (2013.01); *C12N 15/63* (2013.01); *C12N 2740/15043* (2013.01)

(58) Field of Classification Search
CPC .................. C12N 5/0667; C12N 15/63; C12N 2740/15043
See application file for complete search history.

(56) References Cited

FOREIGN PATENT DOCUMENTS

| EP | 2424979 | 11/2010 |
|---|---|---|
| WO | 2010/125527 | 11/2010 |

OTHER PUBLICATIONS

Martinez-Quintanilla et al, "Therapeutic efficacy and fat of bimodal engineered stem cells in malignant brain tumors"; Stem Cells Published Aug. 2013, pp. 1-9. (Year: 2013).*

Ramos et al, An Inducible Caspase 9 Suicide Gene to Improve the Safety of Mesenchymal Stromal Cell Therapies; Stem Cells, Published Jun. 2010, pp. 1-9. (Year: 2010).*

Filippo Rossignoli et al, "Inducible Caspase9-mediated suicide gene for MSC-based cancer gene therapy", Cancer Gene Therapy,Jun. 29, 2018 (Jun. 29, 2018).

Jordi Martinez-Quintanilla et al, "Therapeutic Efficacy and Fate of Bimodal Engineered Stem Cells in Malignant Brain Tumors : Tumor Efficacy and Fate of Therapeutic Stem Cells", Stem Cells., vol. {0} 31, No. {0} 8, Aug. 1, 2013 (Aug. 1, 2013), p. 1706-1714.

Ramos C A et al, "An inducible Caspase 9 suicide gene to improve the safety of mesenchymal stromal cel therapies", Stem Cells, Alphamed Press, Dayton, OH, US, Vol. {0} 28, No. {0} 6, Jun. 1, 2010 (Jun. 1, 2010), p. 1107-1115.

S. W. Kim et al, "Complete Regression of Metastatic Renal Cell Carcinoma by Multiple Injections of Engineered Mesenchymal Stem Cells Expressing Dodecameric TRAIL and HSV-TK", Clinical Cancer Research, vol. {0} 19, No. {0} 2, Nov. 30, 2012 (Nov. 30, 2012), p. 415-427.

C. Quintarelli et al, "Co-expression of cytokine and suicide genes to enhance the activity and safety of tumor-specific cytotoxic T lymphocytes", BLOOD, vol. {0} 110, No. {0} 8, Oct. 15, 2007 (Oct. 15, 2007), p. 2793-2802.

G. Grisendi et al, "Adipose-Derived Mesenchymal Stem Cells as Stable Source of Tumor Necrosis Factor-Related Apoptosis-Inducing Ligand Delivery for Cancer Therapy", Cancer Research, vol. {0} 70, No. {0} 9, May 1, 2010 (May 1, 2010), p. 3718-3729.

Bourgine Paul et al, "Combination of immortalization and inducible death strategies to generate a human mesenchymal stromal cell line with controlled survival", Stem Cell Research, vol. {0} 12, No. {0} 2, Dec. 27, 2013 (Dec. 27, 2013), p. 584-598.

Choi Seung AH et al, "Therapeutic efficacy and safety of TRAIL-producing human adipose tissue-derived mesenchymal stem cells against experimental brainstem glioma.", Neuro-Oncology Jan. 2011, vol. {0} 13, No. {0} 1, Jan. 2011 (Jan. 2011), p. 61-69.

Daniel W. Stuckey et al, "TRAIL on trial: preclinical advances in cancer therapy", Molecular Medicine Today, vol. {0} 19, No. {0} 11, Nov. 1, 2013 (Nov. 1, 2013), p. 685-694.

Yuan et al, "Cell-to-Cell variability in inducible Caspase9-mediated cell death", Cell Death and Disease, 2022, 13:34.

Berger C., Flowers M.E., Warren E.H., Riddell S.R. "Analysis of transgene-specific immune responses that limit the in vivo persistence of adoptively transferred HSV-TK-modified donor T cells after allogeneic hematopoietic cell transplantation." Blood. 2006;107:2294-2302.

* cited by examiner

*Primary Examiner* — Abigail Vanhorn
*Assistant Examiner* — Stephanie L Sullivan
(74) *Attorney, Agent, or Firm* — RANKIN, HILL & CLARK LLP

(57) ABSTRACT

The method to produce conditionally apoptotic cells comprises modifying a cell population with a phenotype attributable to human adipose tissue-derived pericytes (AD-PC) expressing anti-tumor TRAIL introducing a sequence coding a conditional suicide gene (CSG).

6 Claims, 4 Drawing Sheets
Specification includes a Sequence Listing.

METHOD TO PRODUCE CONDITIONALLY APOPTOTIC CELLS

FIELD OF THE INVENTION

The present invention concerns a method to produce cells containing a conditional suicide gene within a cell therapy approach, which can be implemented ex vivo with the condition of a genetic modifications of vehicle cells.

BACKGROUND OF THE INVENTION

It is known that adult progenitor cells, including a cell population with a phenotype attributable to human adipose tissue-derived pericytes (hereafter AD-PC for short), can be used as a vehicle to carry bio-active molecules.

In particular, AD-PCs can carry so-called "death ligands", that is, a family of molecules belonging to the Tumor Necrosis Factor superfamily.

Among these, the Tumor necrosis factor-Related Apoptosis-Inducing Ligand (hereafter TRAIL for short) molecule can induce cell death in diseased tissues, and therefore is particularly interesting for its possible use in certain biomedical fields.

From European patent EP2424979 a method to produce medications for the treatment of tumors is known, which comprises preparing a retroviral vector which encodes a soluble variant of the TRAIL molecule, and which stably transfects adipose pericytes (AD-PC).

AD-PCs that carry TRAIL have shown cytotoxic activity in vitro and in vivo against some tumors and are therefore particularly interesting in the context of cancer treatments.

Furthermore, the expression "conditional suicide gene" (hereafter CSG for short) indicates a genetic element able to induce apoptosis in cells that carry it under specific circumstances.

The CSG is initially contained in a viral particle that is able to infect the recipient cell and thus integrate the coding sequence within its genome.

The CSG can then be processed by the cell and is able to induce apoptosis when specific conditions occur.

These conditions include, for example, but not exclusively, the administration of a specific compound that influences, or is influenced by, the CSG, inducing the death of the cell by apoptosis.

The behavior of the infected cells is not affected by the presence of CSG as long as the apoptotic stimulus is not triggered.

Two common examples of CSG are herpes simplex virus thymidine kinase (hereafter, HSV-TK for short) and cytosine deaminase (hereafter CD for short).

These transgenes give the cell the ability to convert a non-toxic precursor into an active cytotoxic compound that kills the cell itself.

The precursor is Ganciclovir in the case of HSV-TK, or 5-Fluorocytosine in the case of CD.

Another CSG, known as inducible Caspase 9 (hereafter iCasp9 for short), described more recently, is based on the human Caspase 9 sequence.

Its biologically inactive product binds with high affinity to a small biologically inert molecule called AP20187.

The binding of two products of iCasp9 to AP20187 results in their dimerization and activation finally leading the cell to death.

However, this state of the art is affected by some problems.

A first problem is that the safety of treatments that provide to inoculate living cells carrying bioactive molecules in an organism for therapeutic purposes is still being debated.

In particular, the fate of the inoculated cells cannot be controlled in advance.

The main uncertainties concern their potential for uncontrolled expansion, which can cause damage to healthy organs and alterations of physiological functions.

A second problem is that the risk of malign transformations and the development of tumor phenotypes has to be taken into consideration, since it cannot be entirely excluded.

Furthermore, the bioactive molecule carried, such as for example TRAIL, can result unacceptably toxic to the receiving organism, in a way that cannot be determined before the cells are administered.

One purpose of the invention is to improve the state of the art.

Another purpose of the invention is to provide a method to produce conditionally apoptotic cells which allows to improve the safety of a population of TRAIL-producing AD-PCs for antitumor purposes (AD-PC-TRAIL) so that they express a CSG.

Another purpose of the invention is to provide a method to produce conditionally apoptotic cells that allows to improve the safety of the AD-PC-TRAIL, without compromising the anti-tumor action of TRAIL.

Another purpose of the invention is to provide a method to produce conditionally apoptotic cells which allows to obtain the selective self-elimination of the AD-PC-TRAIL, when required, subjecting the AD-PC-TRAIL to a suicide activating agent, thus limiting the occurrence of side effects that are undesirable for the organism and attributable to the AD-PC-TRAIL themselves.

According to one aspect, the invention provides a method to produce conditionally apoptotic cells, according to the characteristics of claim 1.

In another aspect, the invention provides a method to produce conditionally apoptotic cells, which allows to obtain the self-elimination of the AD-PC-TRAIL-CSGs by subjecting them to a suicide activating agent.

In a further aspect, the invention provides a method to produce conditionally apoptotic cells which allows to obtain the efficient, constant and stable production of a viral vector encoding a CSG by means of production lines derived from tumor cells.

According to another aspect of the invention, a cell is provided containing a conditional suicide gene.

BRIEF DESCRIPTION OF THE DRAWINGS

Other characteristics and advantages of the invention will become more apparent from the following description of an embodiment of a method for the production of cells containing a conditional suicide gene within a cell therapy protocol, given as a non-restrictive example with reference to the attached drawings wherein.

DETAILED DESCRIPTION OF A PREFERRED EXAMPLE OF EMBODIMENT

The invention concerns a method to introduce a CSG into AD-PC-TRAIL cells since it has been found it to be capable of inducing suicide.

In a preferred form of the invention, the introduction of CSG can occur by means of a retroviral particle and more specifically lentiviral, as will be described below in an example embodiment, referring to this possibility.

Figure 1:
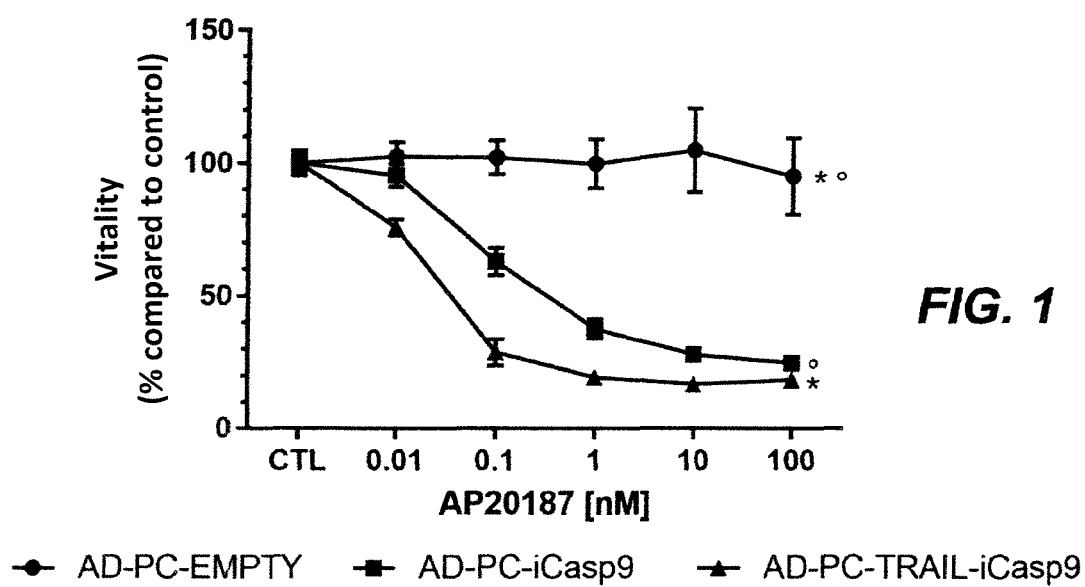
FIG. 1 is a diagram of a dose-response assay on AD-PC, AD-PC expressing iCasp9 (AD-PC-iCasp9) and AD-PC simultaneously expressing TRAIL and iCasp9 (AD-PC-TRAIL-iCasp9)

With reference to FIG. 1, it shows the effect on the vitality of 24 h of incubation with a range of concentrations of AP20187.

The drawing shows a progressive drop in the vitality of both the AD-PC-iCasp9, and also the AD-PC-TRAIL-iCasp9, which reaches 20% at the 100 nM concentration.

Although the slope is more pronounced in the curve representing the AD-PC-TRAIL-iCasp9, both cell populations reach a similar plateau at the 10 nM concentration.

The treatment has no effect on the AD-PC-EMPTY.

Using ANOVA statistical analysis, a statistically significant difference was found among the three groups, characterized by a value of $p<0.0001$ (symbolized by * and ° in the drawing).

The data are represented as mean±Standard deviation (SD).

Figure 2:
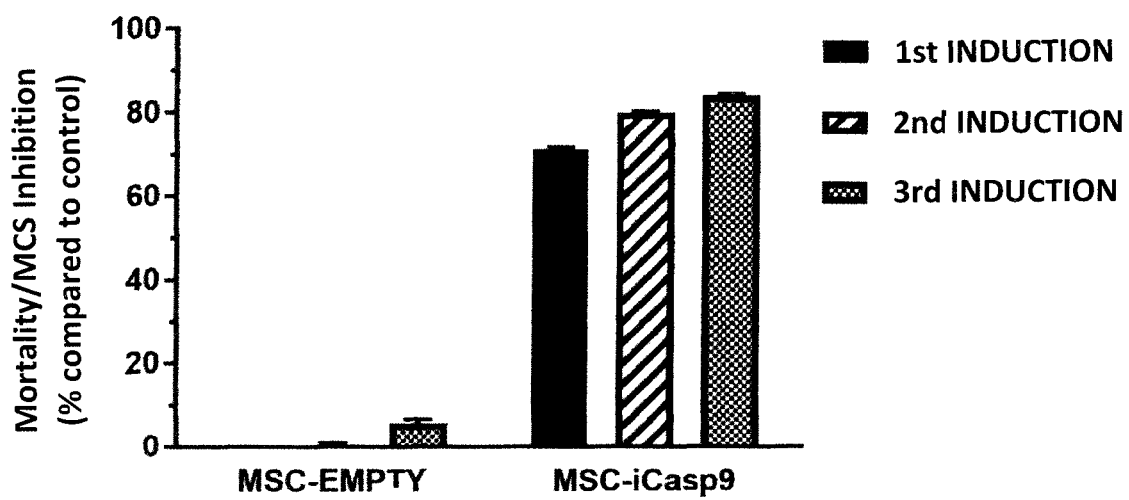
FIG. 2 is a diagram of a suicide induction assay on AD-PC modified with an empty vector (AD-PC-EMPTY) and AD-PC-iCasp9.

With reference to FIG. 2, the cells were treated with 10 nM AP20187 between 1 and 3 times.

In the drawing it can be seen that the first 24 h of incubation bring 71±0.4% of cells in apoptosis and a subsequent identical treatment on the surviving cells results in a mortality of 80±0.3%.

In addition, a further identical treatment improves the suicide rate up to 84±0.3%.

These data show that the treatment can be repeated to eliminate the still vital cells after one treatment.

Using a T-test statistical test, a statistically significant difference was found between the groups characterized by a value of $p<0.01$ (symbolized by * in the drawing).

The data are represented as mean±Standard Mean Error (SEM).

Figure 3:
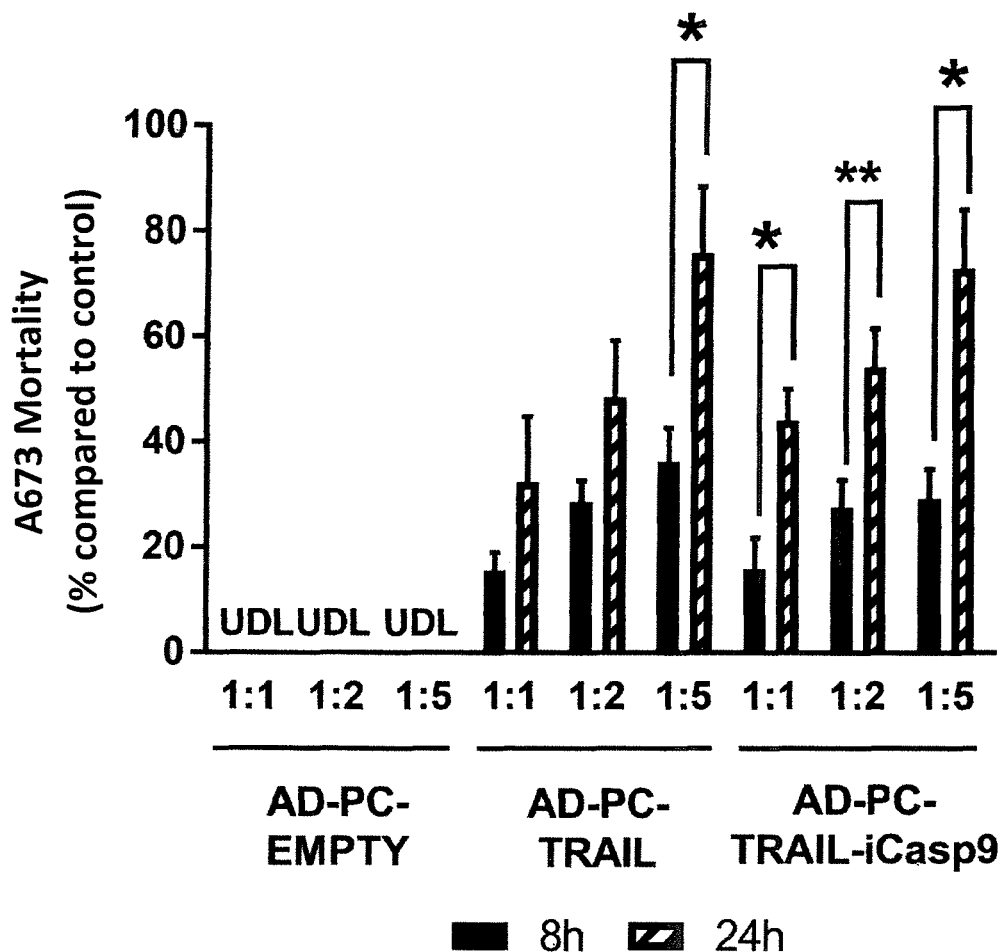
FIG. 3 is a diagram of a co-culture cytotoxicity assay between A673 and AD-PC-EMPTY, AD-PC-TRAIL or AD-PC-TRAIL-iCasp9 cells.

With reference to FIG. 3, the release assay of the $^{51}Cr$ in co-culture shows a similar cytotoxic capacity between AD-PC-TRAIL and AD-PC-TRAIL-iCasp9.

In particular, at the 1:1 ratio, mortality in co-culture with AD-PC-TRAIL increases from 15.5±3.5% after 8 h to 32.4±12.3% after 24 h, at the 1:2 ratio increases from 28.6±4.1% after 8 h to 48.5±10.7% after 24 h, and at the 1:5 ratio increases from 36.3±6.5% after 8 h to 76.0±12.4% after 24 h.

Similarly, in co-culture with AD-PC TRAIL-iCasp9, at the 1:1 ratio, mortality increased from 15.8±6.1% after 8 h to 44.2±5.9% after 24 h, at the 1:2 ratio increases from 27.7±5.2% after 8 h to 54.3±7.3% after 24 h, and at the 1:5 ratio increases from 29.3±5.6% after 8 h to 72.9=11.0% after 24 h.

Using a T-test statistical test, a statistically significant difference was found between the groups characterized by a value of $p<0.01$ (symbolized by * in the drawing) and by an additional value of $p<0.05$ (symbolized by ** in the drawing).

The data are represented as mean±SEM.

Figure 4:
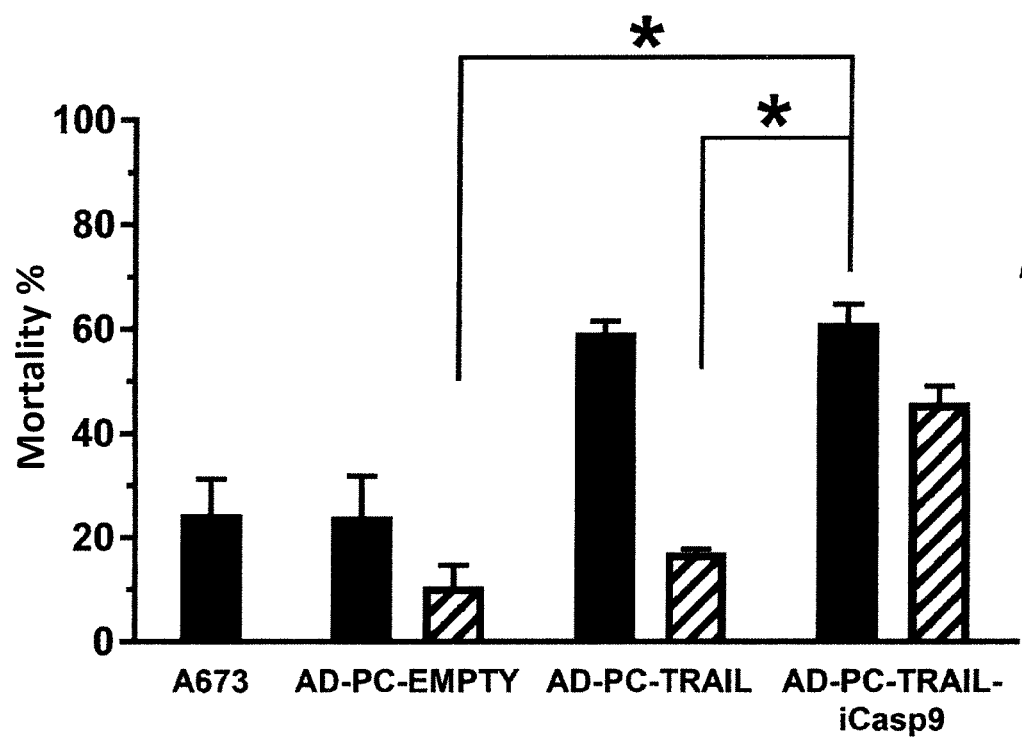
FIG. 4 is a diagram of a combined assay in which AD-PC-EMPTY, AD-PC-TRAIL and AD-PC-TRAIL-iCasp9 are initially used against cells of the A673 tumor line and subsequently induced to suicide after completion of the cytotoxic activity.

With reference to FIG. 4, on the one hand the cytotoxic action of the TRAIL-producing AD-PCs with a mortality of 59.4±2.2% or 61.2±3.6% is confirmed when the A673 tumor cells are co-cultivated respectively with AD-PC-TRAIL or with AD-PC-TRAIL-iCasp9 (baseline mortality of A673 tumor cells: 24.1±6.9%) and, on the other hand, it is again shown that with the proposed protocol the AD-PC-iCasp9 can be addressed to the apoptosis (45.9±3.1%). Using a T-test statistical test a statistically significant difference was found between the groups characterized by a value of $p<0.01$ (symbolized by * in the drawing).

The data are represented as mean±SD.

Example 1

• Creation of the Coding Lentiviral Vector for the CSG iCasp9.

The method to clone the iCasp9 construct into a lentiviral vector is as follows.

The plasmid pMSCV-F-del Casp9.IRES.GFP was purchased from the ADDGENE® company bank (ADDGENE® company plasmid #15567, www.addgene.org/).

The coding fragment for iCasp9 was sub-cloned in a third-generation lentiviral vector (pCCL.PGK.WPRE) which was then used in the following procedures.

• Creation of a Population of AD-PC Expressing CSG iCasp9 in a Stable Manner Starting from a Pre-Existing Population of TRAIL-Producing AD-PCs.

The creation of a population of lentiviruses capable of infecting the cell population of interest represented by the AD-PC-TRAILs is divided into two steps: a first step, based on obtaining a cell line that produces the lentivirus in a transient manner, and a second step with the aim of infecting the target AD-PC and AD-PC-TRAIL cells.

For the transient step, embryonic kidney fibroblasts (293T cells), with about 70% confluency, are transfected with a solution containing 22.5 µg total of plasmid DNA in addition to polycations.

Subsequently, the lentiviral supernatant obtained from 293T cells was collected and used to infect the AD-PC and AD-PC-TRAIL as described below.

AD-PC and AD-PC-TRAIL were seeded at a concentration of $6 \times 10^3/cm^2$ 12 hours before infection.

Then, the culture medium was replaced with the supernatant containing the lentiviral particles supplemented with 6 µg/ml of polybrene and the cells were left in an incubator at 37° C., 5% $CO_2$ for 6 hours.

After the incubation period, the culture medium was replaced with standard culture medium and the infection procedure was repeated identically the following day.

• Confirmation of Successful Infection and Verification of Suicide Capacity.

To confirm the success of the infection and to assess the suicide capacity of the AD-PC-TRAIL-iCasp9, the modified AD-PCs were tested for apoptosis induction after the addition of AP20187 (B/B Homodimerizer, Clontech Laboratories, Inc.) through the MTS metabolic assay (CellTiter 96® AQueous One Solution Cell Proliferation Assay, Promega).

A series of AP20187 concentrations (0.01 nM, 0.1 nM, 1 nM, 10 nM, 100 nM) were tested.

Briefly, for each dimerizer concentration tested, 5000 AD-PC-TRAIL-iCasp9 were seeded in a well of a multi-well plate with 96 wells.

The day after seeding, the culture medium was replaced with fresh medium containing the AP20187 concentration.

After a further 24 hours, the culture plate was analyzed with the Multiskan FC plate reader (Thermo Scientific) following the manufacturer's instructions.

For comparison, the same assay was performed on AD-PC-iCasp9 and AD-PC-EMPTY.

• Verification of the Possibility of Repeatedly Inducing Suicide to Eliminate the AD-PC-iCasp9 that Survived.

In addition, to verify whether the surviving cells had developed resistance to treatment, we proceeded with a triple suicide induction assay.

The AD-PC-EMPTY and AD-PC-iCasp9 were seeded in multi-well plates with 96 wells and incubated with AP20187 10 nM (1st induction).

After 24 h, the mortality rate was determined in some samples through the MTS metabolic assay while the other samples were further incubated with AP20187 10 nM (2nd induction).

After a further 24 h, the second group of samples was assessed for mortality with MTS metabolic assay, while the remaining samples were incubated with AP20187 10 nM for the third time (3rd induction) for 24 h and finally assessed for mortality with MTS metabolic assay.

Results of Example 1

In order to generate a population of TRAIL-producing cells expressing CSG iCasp9, the iCasp9 gene was sub-cloned in a retroviral vector, more specifically a third-generation lentiviral vector used to modify the AD-PC-TRAIL.

The dose-response assay in which the modified cells were exposed to various concentrations of AP20187 confirmed the success of the infection.

Furthermore, the assay showed that AP20187 is able to effectively trigger apoptosis in both the AD-PC-iCasp9 and also the AD-PC-TRAIL-iCasp9 (FIG. 1).

In particular, after 24 hours of treatment an initial decrease in cell vitality was observed when the cells were exposed to a dimerizer concentration equal to 0.01 nM.

The increase in concentration corresponds to an increase in mortality that reaches 80% at a concentration of 100 nM.

The percentage of apoptosis for the AD-PC-TRAIL-iCasp9 reaches a plateau with a concentration of 1 nM.

Furthermore, the double infection did not interfere with the elimination of the modified cells mediated by iCasp9 and in fact 80% of cellular mortality was observed in the twice-infected cells.

In the same experimental setting, the AD-PC-EMPTY are not influenced by the presence of the dimerizing molecule at all concentrations tested.

The surviving AD-PC-iCasp9 after 24 h of incubation with AP20187, were treated again according to the same protocol to determine whether they had developed resistance to treatment.

Repeated administrations showed an increased mortality rate at each administration, from 71% to 84%, and therefore exclude the establishment of a resistance, reinforcing the reliability of the approach (FIG. 2).

Example 2

• Confirmation of the TRAIL-Mediated Cytotoxic Activity of the AD-PC-TRAIL-iCasp9.

To confirm that the TRAIL-mediated cytotoxic activity is not compromised by the presence of the iCasp9 gene, the cytotoxic activity of the AD-PC-TRAIL-iCasp9 was evaluated against the A673 Ewing Sarcoma tumor line in co-culture, through a release assay of 5 Cr and compared with that of the AD-PC-EMPTY and AD-PC-TRAIL.

Briefly, the tumor cells were labeled with $^{51}$Cr and then cultured alone or in co-culture with AD-PC-EMPTY, AD-PC-TRAIL or AD-PC-TRAIL-iCasp9 for 8 h and 24 h at various ratios of target cell and effector cell (1:1, 1:2, 1:5).

The $^{51}$Cr released was detected by the Microbeta2™ 2450 micro-plate counter (Perkin Elmer).

The analysis of the data obtained allowed to correlate the radiation emission with the percentage of dead cells.

Results of Example 2

The release assay of $^{51}$Cr in co-culture demonstrated that the expression of iCasp9 does not influence the cytotoxic activity of the AD-PC-TRAIL, endorsing the feasibility of the combined approach.

As shown in FIG. 3, the AD-PC-TRAIL-iCasp9 are able to eliminate A673 tumor cells with an efficacy very similar to that of the AD-PC-TRAIL.

The effect can be clearly appreciated after 8 h of co-culture and becomes more evident after 24 h.

Furthermore, an increase in the cytotoxic capacity of the AD-PC was observed as the ratio between AD-PC and tumor cells increased, reaching, at the highest ratio, 72.9% mortality of the tumor line.

Example 3

• Combination of Cytotoxicity and Suicide.

The cytotoxicity and suicide assays were combined together in a comprehensive assay to test whether the AD-PC-TRAIL-iCasp9 can be induced to suicide after cytotoxic activity, modeling a possible clinical scenario.

A673 tumor cells were seeded in a 12-well multi-well plate at a density of 6,000 cells/cm$^2$.

The following day, AD-PC-EMPTY, AD-PC-TRAIL and AD-PC-TRAIL-iCasp9 were labeled with CellTrace™ CFSE Proliferation Kit (Thermo Fisher) according to the protocol provided by the manufacturer and seeded in co-culture with A673 cells at the density of 12000 cells/cm$^2$ (1:2 ratio between A673 and AD-PC).

After 24 h of co-culture, AP20187 10 nM was added and the induction lasted 18 h. Subsequently, the cells were labeled with Propidium Iodide 50 µg/ml (Sigma) for 30', collected and evaluated in flow cytometry to determine the percentage of dead cells using a FACSAria™ III (BD Biosciences).

Results of Example 3

The assay combining the TRAIL-mediated cytotoxicity followed by the activation of iCasp9 and consequent suicide induction, summarizes in a simple model the basis of the technical result of the combination of TRAIL with a CSG.

The genetically modified AD-PCs were cultured with the A673 and then induced to suicide after the occurred cytotoxic effect.

The ability of the AD-PC-TRAIL and AD-PC-TRAIL-iCasp9 to induce apoptosis in A673 tumor cells was confirmed with respectively 59% and 61% mortality in the tumor cells after 24 hours (FIG. 4).

Contextually, the specific activation of the apoptosis induced by the dimerizer was observed only in cells expressing iCasp9 (46% of dead cells; see FIG. 4).

It has been found that the invention achieves the intended purposes.

All the elements can be replaced with other technically equivalent ones.

In practice, the substances and quantities used can be modified according to requirements, without departing from the field of protection of the following claims.

The invention claimed is:

1. A method to produce conditionally apoptotic cells, comprising:
    modifying, with the introduction of a sequence coding a conditional suicide gene (CSG), a cell population expressing an anti-tumor soluble tumor necrosis factor-related apoptosis-inducing ligand (TRAIL), infected with a retroviral vector and with a human adipose tissue-derived pericytes (AD-PC) phenotype, wherein said suicide gene is iCasp9, and said cells with a pericytes (PC) phenotype are generated by tissues selected from the group consisting of adipose tissue, placenta, amniotic fluid, dental pulp, muscle tissue, cardiac tissue, umbilical cord, cutaneous tissue, pancreatic tissue, intestinal tissue, and decidual endometrial tissue.

2. The method as in claim 1, wherein said viral vector comprises at least one lentiviral variant.

3. The method as in claim 1, wherein said cell population with a human adipose tissue-derived pericytes (AD-PC) phenotype is infected in a stable way.

4. The method as in claim 1, wherein said retrovirus is produced by a cell line of 293T fibroblasts in a manner selected between a transient manner or a stable manner.

5. The method as in claim 1, wherein said population expressing TRAIL is selected from the group consisting of autologous cells, allogenic cells, human cells, and animal cells.

6. An isolated, modified cell produced by the method as in claim 1.

SEQUENCE LISTING

```
<160> NUMBER OF SEQ ID NOS: 3

<210> SEQ ID NO 1
<211> LENGTH: 8398
<212> TYPE: DNA
<213> ORGANISM: Unknown
<220> FEATURE:
<223> OTHER INFORMATION: iCasp9 Expression vector used

<400> SEQUENCE: 1
caggtggcac ttttcgggga aatgtgcgcg gaacccctat ttgtttattt ttctaaatac      60
attcaaatat gtatccgctc atgagacaat aaccctgata aatgcttcaa taatattgaa     120
aaaggaagag tatgagtatt caacatttcc gtgtcgccct tattcccttt tttgcggcat     180
tttgccttcc tgttttttgct cacccagaaa cgctggtgaa agtaaaagat gctgaagatc     240
agttgggtgc acgagtgggt tacatcgaac tggatctcaa cagcggtaag atccttgaga     300
gttttcgccc cgaagaacgt tttccaatga tgagcacttt taaagttctg ctatgtggcg     360
cggtattatc ccgtattgac gccgggcaag agcaactcgg tcgccgcata cactattctc     420
agaatgactt ggttgagtac tcaccagtca cagaaaagca tcttacggat ggcatgacag     480
taagagaatt atgcagtgct gccataacca tgagtgataa cactgcggcc aacttacttc     540
tgacaacgat cggaggaccg aaggagctaa ccgcttttttt gcacaacatg ggggatcatg     600
taactcgcct tgatcgttgg gaaccggagc tgaatgaagc cataccaaac gacgagcgtg     660
acaccacgat gcctgtagca atggcaacaa cgttgcgcaa actattaact ggcgaactac     720
ttactctagc ttcccggcaa caattaatag actggatgga ggcggataaa gttgcaggac     780
cacttctgcg ctcggccctt ccggctggct ggtttattgc tgataaatct ggagccggtg     840
agcgtgggtc tcgcggtatc attgcagcac tggggccaga tggtaagccc tcccgtatcg     900
tagttatcta cacgacgggg agtcaggcaa ctatggatga acgaaataga cagatcgctg     960
agataggtgc ctcactgatt aagcattggt aactgtcaga ccaagtttac tcatatatac    1020
tttagattga tttaaaactt catttttaat ttaaaaggat ctaggtgaag atcctttttg    1080
ataatctcat gaccaaaatc ccttaacgtg agttttcgtt ccactgagcg tcagaccccg    1140
tagaaaagat caaaggatct tcttgagatc ctttttttct gcgcgtaatc tgctgcttgc    1200
aaacaaaaaa accaccgcta ccagcggtgg tttgtttgcc ggatcaagag ctaccaactc    1260
tttttccgaa ggtaactggc ttcagcagag cgcagatacc aaatactgtc cttctagtgt    1320
agccgtagtt aggccaccac ttcaagaact ctgtagcacc gcctacatac ctcgctctgc    1380
taatcctgtt accagtggct gctgccagtg gcgataagtc gtgtcttacc gggttggact    1440
caagacgata gttaccggat aaggcgcagc ggtcgggctg aacggggggt tcgtgcacac    1500
agcccagctt ggagcgaacg acctacaccg aactgagata cctacagcgt gagctatgag    1560
aaagcgccac gcttcccgaa gggagaaagg cggacaggta tccggtaagc ggcagggtcg    1620
gaacaggaga gcgcacgagg gagcttccag ggggaaacgc ctggtatctt tatagtcctg    1680
tcgggtttcg ccacctctga cttgagcgtc gatttttgtg atgctcgtca ggggggcgga    1740
gcctatgaaa aacgccagc aacgcggcct ttttacggtt cctggccttt tgctggcctt    1800
```

```
ttgctcacat gttctttcct gcgttatccc ctgattctgt ggataaccgt attaccgcct    1860
ttgagtgagc tgataccgct cgccgcagcc gaacgaccga gcgcagcgag tcagtgagcg    1920
aggaagcgga agagcgccca atacgcaaac cgcctctccc cgcgcgttgg ccgattcatt    1980
aatgcagctg gcacgacagg tttcccgact ggaaagcggg cagtgagcgc aacgcaatta    2040
atgtgagtta gctcactcat taggcacccc aggctttaca ctttatgctt ccggctcgta    2100
tgttgtgtgg aattgtgagc ggataacaat ttcacacagg aaacagctat gaccatgatt    2160
acgccaagcg cgcaattaac cctcactaaa gggaacaaaa gctggagctg caagcttggc    2220
cattgcatac gttgtatcca tatcataata tgtacattta tattggctca tgtccaacat    2280
taccgccatg ttgacattga ttattgacta gttattaata gtaatcaatt acgggtcat    2340 tagttcatag cccatatatg gagttccgcg ttacataact tacggtaaat ggcccgcctg    2400
gctgaccgcc caacgacccc cgcccattga cgtcaataat gacgtatgtt cccatagtaa    2460
cgccaatagg gactttccat tgacgtcaat gggtggagta tttacggtaa actgcccact    2520
tggcagtaca tcaagtgtat catatgccaa gtacgccccc tattgacgtc aatgacggta    2580
aatggcccgc ctggcattat gcccagtaca tgaccttatg ggactttcct acttggcagt    2640
acatctacgt attagtcatc gctattacca tggtgatgcg gttttggcag tacatcaatg    2700
ggcgtggata gcggtttgac tcacggggat ttccaagtct ccaccccatt gacgtcaatg    2760
ggagtttgtt ttggcaccaa aatcaacggg actttccaaa atgtcgtaac aactccgccc    2820
cattgacgca aatgggcggt aggcgtgtac ggtgggaggt ctatataagc agagctcgtt    2880
tagtgaaccg ggtctctct ggttagacca gatctgagcc tgggagctct ctggctaact    2940
agggaaccca ctgcttaagc ctcaataaag cttgccttga gtgcttcaag tagtgtgtgc    3000
ccgtctgttg tgtgactctg gtaactagag atccctcaga cccttttagt cagtgtggaa    3060
aatctctagc agtggcgccc gaacagggac ctgaaagcga aagggaaacc agagctctct    3120
cgacgcagga ctcggcttgc tgaagcgcgc acggcaagag gcgaggggcg cgactggtg    3180 agtacgccaa aaattttgac tagcggaggc tagaaggaga gagatgggtg cgagagcgtc    3240
agtattaagc gggggagaat tagatcgcga tgggaaaaaa ttcggttaag gccaggggga    3300
aagaaaaaat ataaattaaa acatatagta tgggcaagca gggagctaga acgattcgca    3360
gttaatcctg gcctgttaga acatcagaa ggctgtagac aaatactggg acagctacaa    3420
ccatcccttc agacaggatc agaagaactt agatcattat ataatacagt agcaaccctc    3480
tattgtgtgc atcaaaggat agagataaaa gacaccaagg aagctttaga caagatagag    3540
gaagagcaaa acaaaagtaa gaccaccgca cagcaagcgg ccgctgatct tcagacctgg    3600
aggaggagat atgagggaca attggagaag tgaattatat aaatataaag tagtaaaaat    3660
tgaaccatta ggagtagcac ccaccaaggc aaagagaaga gtggtgcaga gagaaaaaag    3720
agcagtggga ataggagctt tgttccttgg gttcttggga gcagcaggaa gcactatggg    3780
cgcagcctca atgacgctga cggtacaggc cagacaatta ttgtctggta tagtgcagca    3840
gcagaacaat ttgctgaggg ctattgaggc gcaacagcat ctgttgcaac tcacagtctg    3900
gggcatcaag cagctccagg caagaatcct ggctgtggaa agatacctaa aggatcaaca    3960
gctcctgggg atttggggtt gctctggaaa actcatttgc accactgctg tgccttggaa    4020
tgctagttgg agtaataaat ctctggaaca gatttggaat cacacgacct ggatggagtg    4080
ggacagagaa attaacaatt acacaagctt aatacactcc ttaattgaag aatcgcaaaa    4140
ccagcaagaa aagaatgaac aagaattatt ggaattagat aaatgggcaa gtttgtggaa    4200
```

```
ttggtttaac ataacaaatt ggctgtggta tataaaatta ttcataatga tagtaggagg    4260
cttggtaggt ttaagaatag tttttgctgt actttctata gtgaatagag ttaggcaggg    4320
atattcacca ttatcgtttc agacccacct cccaaccccg aggggacccg acaggcccga    4380
aggaatagaa gaagaaggtg gagagagaga cagagacaga tccattcgat tagtgaacgg    4440
atctcgacgg tatcggttaa cttttaaaag aaaaggggggg attgggggt acagtgcagg    4500 ggaaagaata gtagacataa tagcaacaga catacaaact aaagaattac aaaaacaaat    4560
tacaaaaatt caaaattta tcgatcacga gactagcctc gagaagcttg ataattcgat    4620
aattcccacg gggttgggt tgcgcctttt ccaaggcagc cctgggtttg cgcagggacg    4680
cggctgctct gggcgtggtt ccgggaaacg cagcggcgcc gaccctgggt ctcgcacatt    4740
cttcacgtcc gttcgcagcg tcacccggat cttcgccgct acccttgtgg gccccccggc    4800
gacgcttcct gctccgcccc taagtcggga aggttccttg cggttcgcgg cgtgccggac    4860
gtgacaaacg gaagccgcac gtctcactag taccctcgca gacggacagc gccagggagc    4920
aatggcagcg cgccgaccgc gatgggctgt ggccaatagc ggctgctcag cggggcgcgc    4980
cgagagcagc ggccgggaag gggcggtgcg ggaggcgggg tgtggggcgg tagtgtgggc    5040
cctgttcctg cccgcgcggt gttccgcatt ctgcaagcct ccggagcgca cgtcggcagt    5100
cggctccctc gttgaccgaa tcaccgacct ctctccccag ggggatcatc gcggccgagg    5160
caggccacgc gtatgctcga gggagtgcag gtggagacta tctcccagg agacgggcgc    5220 accttcccca agcgcggcca gacctgcgtg gtgcactaca ccgggatgct tgaagatgga    5280
aagaaagttg attcctcccg ggacagaaac aagccctta agtttatgct aggcaagcag    5340
gaggtgatcc gaggctggga agaagggtt gcccagatga gtgtgggtca gagagccaaa    5400
ctgactatat ctccagatta tgcctatggt gccactgggc acccaggcat catcccacca    5460
catgccactc tcgtcttcga tgtggagctt ctaaaactgg aatctggcgg tggatccgga    5520
gtcgacggat ttggtgatgt cggtgctctt gagagtttga ggggaaatgc agatttggct    5580
tacatcctga gcatggagcc ctgtggccac tgcctcatta tcaacaatgt gaacttctgc    5640
cgtgagtccg ggctccgcac ccgcactggc tccaacatcg actgtgagaa gttgcggcgt    5700
cgcttctcct cgctgcattt catggtggag gtgaagggcg acctgactgc aagaaaatg    5760 gtgctggctt tgctggagct ggcgcggcag gaccacggtg ctctgactg ctgcgtggtg    5820 gtcattctct ctcacggctg tcaggccagc cacctgcagt tcccaggggc tgtctacggc    5880
acagatggat gccctgtgtc ggtcgagaag attgtgaaca tcttcaatgg gaccagctgc    5940
cccagcctgg gagggaagcc caagctcttt ttcatccagg cctgtggtgg ggagcagaaa    6000
gaccatgggt tgaggtggc ctccacttcc cctgaagacg agtcccctgg cagtaacccc    6060
gagccagatg ccacccgtt ccaggaaggt ttgaggacct tcgaccagct ggacgccata    6120 tctagttgc ccacccag tgacatcttt gtgtcctact ctactttccc aggttttgtt    6180
tcctggaggg accccaagag tggctcctgg tacgttgaga ccctggacga catctttgag    6240
cagtgggctc actctgaaga cctgcagtcc ctcctgctta gggtcgctaa tgctgtttcg    6300
gtgaaaggga tttataaaca gatgcctggt tgctttaatt tcctccggaa aaaacttttc    6360
tttaaaacat cagtcgacta tccgtacgac gtaccagact acgcactcga ctaaacgcgt    6420
gcggccgcgg ccgagcaggc cggatcctct agctagagtc gacaatcaac ctctggatta    6480
caaaatttgt gaaagattga ctggtattct taactatgtt gctccttta cgctatgtgg    6540
```

| | |
|---|---:|
| atacgctgct ttaatgccxt tgtatcatgc tattgcttcc cgtatggctt tcattttctc | 6600 |
| ctccttgtat aaatcctggt tgctgtctct ttatgaggag ttgtggcccg ttgtcaggca | 6660 |
| acgtggcgtg gtgtgcactg tgtttgctga cgcaaccccc actggttggg gcattgccac | 6720 |
| cacctgtcag ctccttttccg ggactttcgc tttccccctc cctattgcca cggcggaact | 6780 |
| catcgccgcc tgccttgccc gctgctggac aggggctcgg ctgttgggca ctgacaattc | 6840 |
| cgtggtgttg tcggggaagc tgacgtcctt ccatggctg ctcgcctgtg ttgccacctg | 6900 |
| gattctgcgc gggacgtcct tctgctacgt cccttcggcc ctcaatccag cggaccttcc | 6960 |
| ttcccgcggc ctgctgccgg ctctgcggcc tcttccgcgt cttcgccttc gccctcagac | 7020 |
| gagtcggatc tcccttggg ccgcctcccc gcctggaatt cgagctcggt acctttaaga | 7080 |
| ccaatgactt acaaggcagc tgtagatctt agccactttt taaaagaaaa ggggggactg | 7140 |
| gaagggctaa ttcactccca acgaagacaa gatctgcttt ttgcttgtac tgggtctctc | 7200 |
| tggttagacc agatctgagc ctgggagctc tctggctaac tagggaaccc actgcttaag | 7260 |
| cctcaataaa gcttgccttg agtgcttcaa gtagtgtgtg cccgtctgtt gtgtgactct | 7320 |
| ggtaactaga gatccctcag acccttttag tcagtgtgga aaatctctag cagtagtagt | 7380 |
| tcatgtcatc ttattattca gtatttataa cttgcaaaga atgaatatc agagagtgag | 7440 |
| aggaacttgt ttattgcagc ttataatggt tacaaataaa gcaatagcat cacaaatttc | 7500 |
| acaaataaag catttttttc actgcattct agttgtggtt tgtccaaact catcaatgta | 7560 |
| tcttatcatg tctggctcta gctatcccgc ccctaactcc gcccagttcc gcccattctc | 7620 |
| cgccccatgg ctgactaatt ttttttattt atgcagaggc cgaggccgcc tcggcctctg | 7680 |
| agctattcca gaagtagtga ggaggctttt ttggaggcct aggcttttgc gtcgagacgt | 7740 |
| acccaattcg ccctatagtg agtcgtatta cgcgcgctca ctggccgtcg ttttacaacg | 7800 |
| tcgtgactgg gaaaaccctg gcgttaccca acttaatcgc cttgcagcac atccccctttt | 7860 |
| cgccagctgg cgtaatagcg aagaggcccg caccgatcgc ccttcccaac agttgcgcag | 7920 |
| cctgaatggc gaatggcgcg acgcgccctg tagcggcgca ttaagcgcgg cgggtgtggt | 7980 |
| ggttacgcgc agcgtgaccg ctacacttgc cagcgcccta gcgcccgctc ctttcgcttt | 8040 |
| cttcccttcc tttctcgcca cgttcgccgg ctttccccgt caagctctaa atcggggggct | 8100 |
| ccctttaggg ttccgattta gtgctttacg gcacctcgac cccaaaaaac ttgattaggg | 8160 |
| tgatggttca cgtagtgggc catcgccctg atagacggtt tttcgccctt tgacgttgga | 8220 |
| gtccacgttc tttaatagtg gactcttgtt ccaaactgga acaacactca acctatctc | 8280 |
| ggtctattct tttgatttat aagggatttt gccgatttcg gcctattggt taaaaaatga | 8340 |
| gctgatttaa caaaaattta acgcgaattt taacaaaata ttaacgttta catttccc | 8398 |

<210> SEQ ID NO 2
<211> LENGTH: 1242
<212> TYPE: DNA
<213> ORGANISM: Unknown
<220> FEATURE:
<223> OTHER INFORMATION: Nucleotidic sequence of iCasp9 gene

<400> SEQUENCE: 2

| | |
|---|---:|
| atgctcgagg gagtgcaggt ggagactatc tccccaggag acgggcgcac cttccccaag | 60 |
| cgcggccaga cctgcgtggt gcactacacc gggatgcttg aagatggaaa gaaagttgat | 120 |
| tcctcccggg acagaaacaa gcccttaag tttatgctag gcaagcagga ggtgatccga | 180 |
| ggctgggaag aagggggttgc ccagatgagt gtgggtcaga gagccaaact gactatatct | 240 |

```
ccagattatg cctatggtgc cactgggcac ccaggcatca tcccaccaca tgccactctc   300
gtcttcgatg tggagcttct aaaactggaa tctggcggtg gatccggagt cgacggattt   360
ggtgatgtcg gtgctcttga gagtttgagg ggaaatgcag atttggctta catcctgagc   420
atggagccct gtggccactg cctcattatc aacaatgtga acttctgccg tgagtccggg   480
ctccgcaccc gcactggctc caacatcgac tgtgagaagt tgcggcgtcg cttctcctcg   540
ctgcatttca tggtggaggt gaagggcgac ctgactgcca gaaaatggt gctggctttg   600 ctggagctgg cgcggcagga ccacggtgct ctggactgct gcgtggtggt cattctctct   660
cacggctgtc aggccagcca cctgcagttc caggggctg tctacggcac agatggatgc   720
cctgtgtcgg tcgagaagat tgtgaacatc ttcaatggga ccagctgccc cagcctggga   780
gggaagccca gctctttttt catccaggcc tgtggtgggg agcagaaaga ccatgggttt   840
gaggtggcct ccacttcccc tgaagacgag tcccctggca gtaaccccga gccagatgcc   900 acccgttcc aggaaggttt gaggaccttc gaccagctgg acgccatatc tagtttgccc   960
acacccagtg acatctttgt gtcctactct actttcccag ttttgtttc ctggagggac   1020 cccaagagtg gctcctggta cgttgagacc ctggacgaca tctttgagca gtgggctcac   1080
tctgaagacc tgcagtccct cctgcttagg gtcgctaatg ctgtttcggt gaagggatt   1140 tataaacaga tgcctggttg ctttaatttc ctccggaaaa aactttttctt taaaacatca   1200 gtcgactatc cgtacgacgt accagactac gcactcgact aa                     1242
```

<210> SEQ ID NO 3  
<211> LENGTH: 413  
<212> TYPE: PRT  
<213> ORGANISM: Unknown  
<220> FEATURE:  
<223> OTHER INFORMATION: Protein sequence of iCasp9

<400> SEQUENCE: 3

```
Met Leu Glu Gly Val Gln Val Glu Thr Ile Ser Pro Gly Asp Gly Arg
1               5                   10                  15

Thr Phe Pro Lys Arg Gly Gln Thr Cys Val Val His Tyr Thr Gly Met
            20                  25                  30

Leu Glu Asp Gly Lys Lys Val Asp Ser Ser Arg Asp Arg Asn Lys Pro
        35                  40                  45

Phe Lys Phe Met Leu Gly Lys Gln Glu Val Ile Arg Gly Trp Glu Glu
    50                  55                  60

Gly Val Ala Gln Met Ser Val Gly Gln Arg Ala Lys Leu Thr Ile Ser
65                  70                  75                  80

Pro Asp Tyr Ala Tyr Gly Ala Thr Gly His Pro Gly Ile Ile Pro Pro
                85                  90                  95

His Ala Thr Leu Val Phe Asp Val Glu Leu Leu Lys Leu Glu Ser Gly
            100                 105                 110

Gly Gly Ser Gly Val Asp Gly Phe Gly Asp Val Gly Ala Leu Glu Ser
        115                 120                 125

Leu Arg Gly Asn Ala Asp Leu Ala Tyr Ile Leu Ser Met Glu Pro Cys
    130                 135                 140

Gly His Cys Leu Ile Ile Asn Asn Val Asn Phe Cys Arg Glu Ser Gly
145                 150                 155                 160

Leu Arg Thr Arg Thr Gly Ser Asn Ile Asp Cys Glu Lys Leu Arg Arg
                165                 170                 175

Arg Phe Ser Ser Leu His Phe Met Val Glu Val Lys Gly Asp Leu Thr
```

```
                        180                 185                 190
Ala Lys Lys Met Val Leu Ala Leu Leu Glu Leu Ala Arg Gln Asp His
        195                 200                 205

Gly Ala Leu Asp Cys Cys Val Val Ile Leu Ser His Gly Cys Gln
        210                 215                 220

Ala Ser His Leu Gln Phe Pro Gly Ala Val Tyr Gly Thr Asp Gly Cys
225                 230                 235                 240

Pro Val Ser Val Glu Lys Ile Val Asn Ile Phe Asn Gly Thr Ser Cys
            245                 250                 255

Pro Ser Leu Gly Gly Lys Pro Lys Leu Phe Phe Ile Gln Ala Cys Gly
            260                 265                 270

Gly Glu Gln Lys Asp His Gly Phe Glu Val Ala Ser Thr Ser Pro Glu
            275                 280                 285

Asp Glu Ser Pro Gly Ser Asn Pro Glu Pro Asp Ala Thr Pro Phe Gln
            290                 295                 300

Glu Gly Leu Arg Thr Phe Asp Gln Leu Asp Ala Ile Ser Ser Leu Pro
305                 310                 315                 320

Thr Pro Ser Asp Ile Phe Val Ser Tyr Ser Thr Phe Pro Gly Phe Val
                325                 330                 335

Ser Trp Arg Asp Pro Lys Ser Gly Ser Trp Tyr Val Glu Thr Leu Asp
                340                 345                 350

Asp Ile Phe Glu Gln Trp Ala His Ser Glu Asp Leu Gln Ser Leu Leu
            355                 360                 365

Leu Arg Val Ala Asn Ala Val Ser Val Lys Gly Ile Tyr Lys Gln Met
    370                 375                 380

Pro Gly Cys Phe Asn Phe Leu Arg Lys Lys Leu Phe Phe Lys Thr Ser
385                 390                 395                 400

Val Asp Tyr Pro Tyr Asp Val Pro Asp Tyr Ala Leu Asp
            405                 410
```